(12) United States Patent
Mollenauer

(10) Patent No.: US 7,396,356 B2
(45) Date of Patent: Jul. 8, 2008

(54) COMBINED DISSECTING, CAUTERIZING, AND STAPLING DEVICE

(75) Inventor: Kenneth H. Mollenauer, Saratoga, CA (US)

(73) Assignee: Starion Instruments Corporation, Sunnyvale, CA (US)

( * ) Notice: Subject to any disclaimer, the term of this patent is extended or adjusted under 35 U.S.C. 154(b) by 390 days.

(21) Appl. No.: 10/995,630

(22) Filed: Nov. 22, 2004

(65) Prior Publication Data
US 2005/0072827 A1 Apr. 7, 2005

Related U.S. Application Data

(63) Continuation of application No. 10/336,385, filed on Jan. 2, 2003, now Pat. No. 6,821,273, which is a continuation-in-part of application No. 10/037,625, filed on Jan. 3, 2002, now Pat. No. 6,602,252.

(51) Int. Cl.
*A61B 18/18* (2006.01)
(52) U.S. Cl. .............................. 606/51; 606/45; 606/46
(58) Field of Classification Search ................... 606/41, 606/45, 46, 48–52, 4
See application file for complete search history.

(56) References Cited

U.S. PATENT DOCUMENTS

| 4,516,574 | A | 5/1985 | Hewes, Jr. |
|---|---|---|---|
| 4,654,024 | A | 3/1987 | Crittenden et al. |
| 5,443,463 | A | 8/1995 | Stern et al. |
| 5,445,638 | A | 8/1995 | Rydell et al. |
| 5,527,313 | A | 6/1996 | Scott et al. |
| 5,531,744 | A | 7/1996 | Nardella et al. |
| 5,624,452 | A | 4/1997 | Yates |
| 5,810,811 | A | 9/1998 | Yates |
| 6,003,517 | A | 12/1999 | Sheffield |
| 6,024,741 | A | 2/2000 | Williamson |
| 6,086,586 | A * | 7/2000 | Hooven .................. 606/50 |
| 6,202,914 | B1 | 3/2001 | Geiste et al. |
| 6,821,273 | B2 * | 11/2004 | Mollenauer ............ 606/28 |
| 6,926,716 | B2 * | 8/2005 | Baker et al. ............ 606/51 |
| 7,041,102 | B2 * | 5/2006 | Truckai et al. ......... 606/51 |

FOREIGN PATENT DOCUMENTS

WO  WO 01/12090  2/2001

* cited by examiner

*Primary Examiner*—Michael Peffley
(74) *Attorney, Agent, or Firm*—K. David Crockett, Esq.; Crockett & Crockett

(57) ABSTRACT

A medical device for simultaneously cutting tissue with a heating element, cauterizing the tissue with sealing elements, and stapling the tissue together. The heating elements comprise bipolar RF electrodes.

12 Claims, 10 Drawing Sheets

COMBINED DISSECTING, CAUTERIZING, AND STAPLING DEVICE

This application is a continuation of U.S. application Ser. No. 10/336,385, filed Jan. 2, 2003, now U.S. Pat. No. 6,821,273 which is a continuation-in-part of U.S. application Ser. No. 10/037,625 filed on Jan. 3, 2002, now U.S. Pat. No. 6,602,252.

FIELD OF THE INVENTION

The devices described below relate to instruments and methods for sealing, joining, and cutting tissue.

BACKGROUND OF THE INVENTION

Many surgical procedures require that body lumens and other tissue be cut and sealed. It is sometimes desirable to close the lumen ends with staples or clips and then to cauterize the tissue at or near the incision to prevent bleeding.

These procedures are frequently used in laparoscopic surgery. For example, one bowel resection procedure involves stapling each end of the colon closed, cutting the colon with a razor or scalpel, and then cauterizing the closed ends with heating elements. Various procedures and devices have been created to perform these tasks more efficiently.

Yates, Hemostatic Surgical Cutting or Stapling Instrument, U.S. Pat. No. 5,624,452 (Apr. 29, 1998), discloses a laparoscopic stapler that uses two rows of staples aligned parallel to each other, with each series of staples aligned parallel to its jaw members. A razor is disposed between the rows of staples, to cut the tissue, and two parallel heating elements are disposed to either side of the razor to cauterize either side of the wound.

For operations which require dividing and stapling large body vessels, such as the colon, bleeding can be greatly reduced vis-à-vis the stapler and cutter of the above references with the devices and methods disclosed below.

SUMMARY

The methods and devices described below combine a stapler, a thermal cutting element, and cauterizing elements all in the same instrument. On the outer edge of the device run parallel rows of staples oriented so that they are parallel to the length of the jaws. Inside the rows of staplers are two parallel rows of sealing elements used for cauterization. In the center is a cutting element used to separate tissue.

The combined stapler and triple-wire instrument is also referred to as a laparoscopic dissecting instrument. The laparoscopic dissecting instrument is useful for performing a variety of surgical procedures, including laparoscopic colectomies and laparoscopic appendectomies.

DETAILED DESCRIPTION OF THE INVENTIONS

Figure 1:
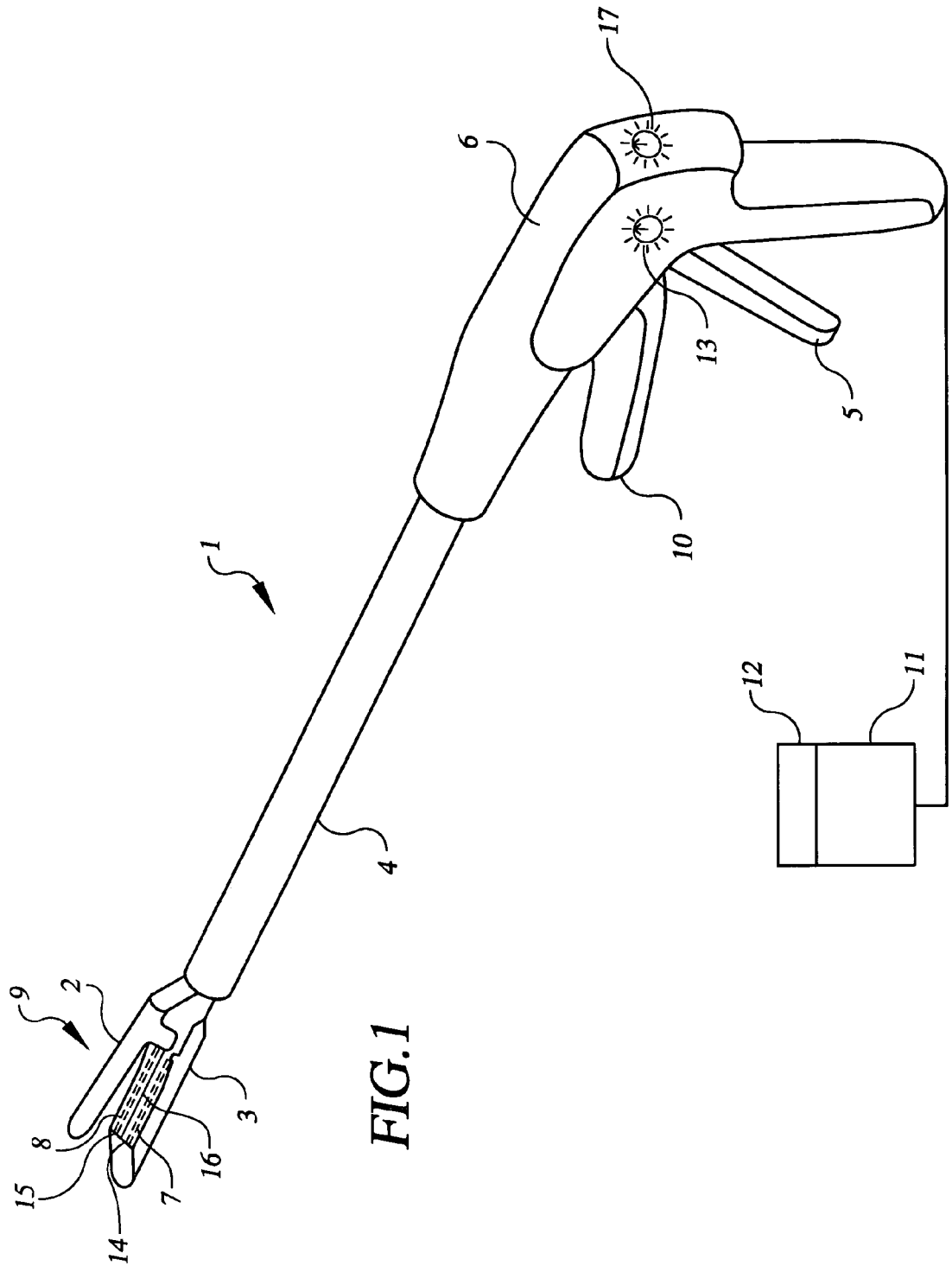
FIG. 1 illustrates the overall laparoscopic dissecting instrument.

FIG. 1 illustrates the overall laparoscopic surgical instrument 1. On the distal end of the instrument are a first, or superior, jaw 2 and a second, or inferior, jaw 3 rotatably mounted to a rigid insertion section of rod, or tube 4, adapted for insertion into a laparoscopic work space. The jaws are also operably connected, through the insertion rod 4, to a grasping lever 5 on the proximal handle, or handle section, 6 of the instrument. When the grasping lever 5 is depressed, the superior jaw 2 will close on the inferior jaw 3 with a force proportionate to the distance the grasping lever 5 is depressed. When the grasping lever 5 is released the jaws will disengage, releasing their grip. In addition, a mechanism allows the surgeon to lock the jaws in the closed position.

Disposed within the inferior jaw 3 are two rows of staples, a left row of staples 7 and a right row of staples 8, that run parallel to the longitudinal axis of the inferior jaw 3. Each row of staples may comprise multiple rows of staples. The staples comprise standard surgical staples, though they may be surgical clips when the laparoscopic surgical instrument 1 is used for different procedures, such as ligation of blood vessels. A stapler mechanism on the stapler head 9 is operably connected to a stapler lever 10 such that when the stapler lever 10 is depressed the staples 7 are ejected from the cartridge and pushed through any body tissue proximate to the cartridge. Any tissue inside the jaws will then be stapled together.

Disposed just inside the two rows of staples 7 and 8 are two parallel rows of sealing elements used to heat or cauterize tissue. A sealing element comprises a heating element that can be raised to a temperature sufficient to cauterize and seal tissue. Electric current is supplied to the sealing elements from an electric current source 11 and regulated by one or more control boxes 12, all of which are operated by the surgeon. The current source 11 may be an AC to DC power converter plugged into an outlet, or may be one or more batteries. A left control dial 13, or controller, controls the temperature of a left sealing element 14 by adjusting the current flow though the left sealing element. The left control dial 13 is located on the left side of the handle 6 and is operably connected to the left sealing element 14 and to the power source 11. A right sealing element 15 is similarly connected to the current source 11. A right control dial, or controller, controls the temperature of the right sealing element 15 by adjusting the current flow through the right sealing element. The right control dial is located on the right side of the handle 6 and is operably connected to the right sealing element 15 and to the power source 11. Each control dial can be independently operated to control the amount of heat applied through each individual sealing element. Alternatively, the control dials may be formed with only "on" and "off" positions so that the temperature of the sealing elements remains set at a level determined by the manufacturer. The control dials may be replaced with levers, buttons, switches, or other suitable mechanisms to control how much, if any, heat is applied to the heating elements. The control mechanisms may be located on the proximal handle 6, as shown, or on the control box 12 or current source 11.

Disposed along the center of the grasping face of the inferior jaw 3 is a cutting element 16 used to sever or cut tissue. A cutting element comprises a heating element that can be heated to a temperature sufficient to sever tissue. The cutting element 16 is operably connected to a cutting element control dial 17, or controller, located on the back of the proximal handle 6, and to the power source 11. The cutting element control dial 17, operably connected to the power source 11 and the cutting element 16, controls the temperature of the cutting element 16. Alternatively, the cutting element control dial may be formed with only "on" and "off" positions so that the temperature of the sealing elements remains set at a level determined by the manufacturer. The cutting element control dial 17 may be replaced with any suitable control mechanism for adjusting temperature, such as buttons, levers, or switches.

Figure 2:
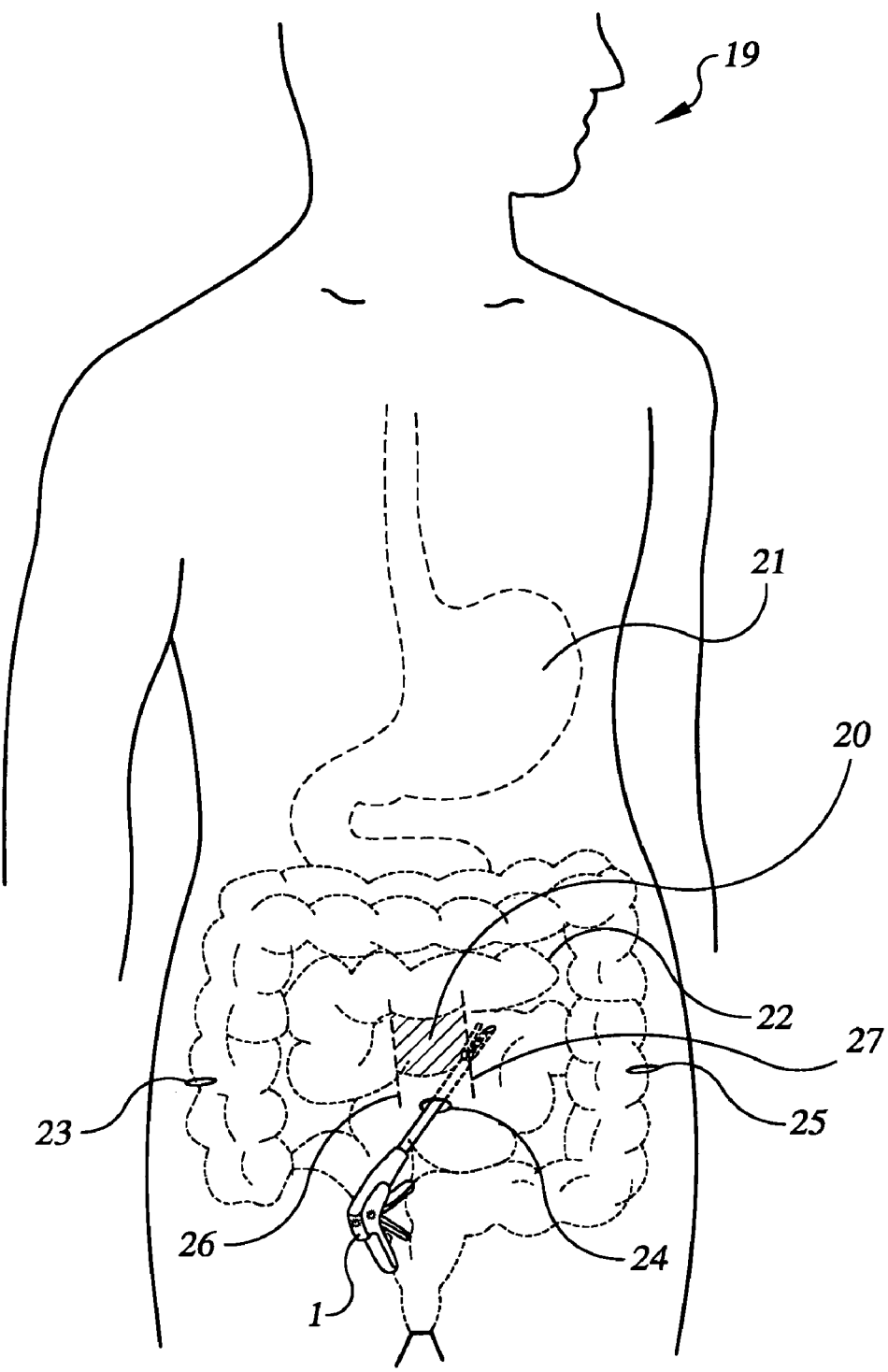
FIG. 2 shows a patient with a diseased section of colon that must be surgically removed and illustrates surgical entry points typically used in a colectomy.

FIGS. 2 through 8 show how the surgical instrument 1 is used in a typical laparoscopic colectomy, or bowel resection. FIG. 2 shows a patient 19 with a diseased section of colon 20, shown with hatch marks, which must be surgically removed. The stomach 21 and large intestine 22 are shown for reference to indicate their position inside the body. A surgeon begins the operation by making incisions at one or more points 23, 24, and 25. One of the incisions is used to insert the laparoscopic dissecting instrument 1 into the abdomen and the other incisions are typically used to insert other devices used in the surgery. The surgeon then uses the laparoscopic dissecting instrument 1 to first cut and then remove the diseased section of colon from the body. Dashed lines 26 and 27 show where the surgeon cuts the colon to remove the diseased portion 20.

Figure 3:
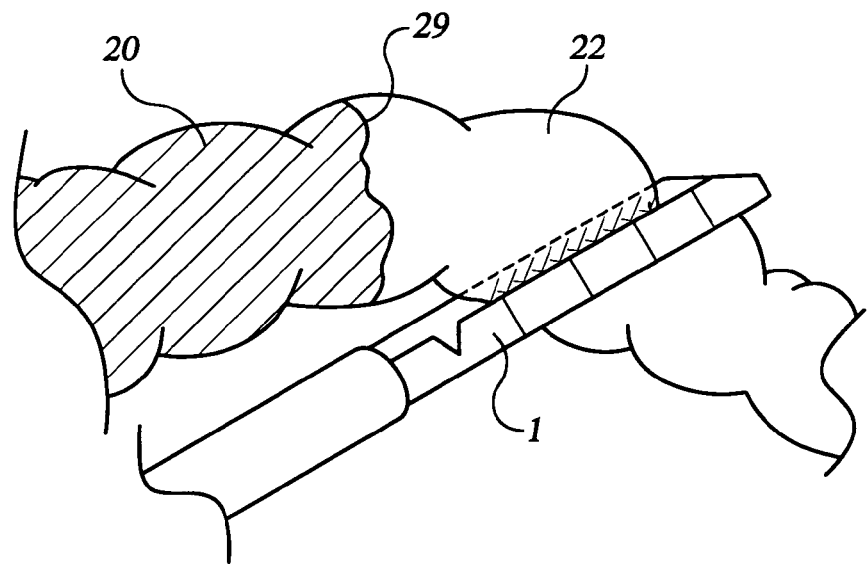
FIG. 3 shows the jaws of the laparoscopic dissecting instrument performing a cut and seal procedure on a section of colon.

FIG. 3 shows the jaws of the laparoscopic dissecting instrument 1 performing a cut and seal procedure on a section of colon 22 at cut line 27 of FIG. 2. As shown in FIG. 3, the instrument 1 firmly grasps the colon at a point relatively far from the section of diseased colon 20, which is shown with hatch marks beginning at demarcation line 29. The left and right sealing elements are heated to the point where the tissue is cauterized to prevent bleeding and leakage of fluids. Typically, the left and right sealing elements are heated to a temperature range of 45° to 99° Celsius. However, due to significant heat transfer losses the sealing elements may be operated above 99° Celsius so that the tissue experiences a temperature of about 95° to 99° Celsius. At those temperatures the tissue is cauterized and sealed fairly quickly, over a few seconds, but not severed.

After heat sealing, the staples are fired or deployed to seal off the two sections of colon. Alternatively, the staples are fired at the same time the tissue is heat sealed. Next, the cutting element is elevated to a temperature high enough to cause the tissue to separate, thus severing the two sections of colon. Alternatively, the staples are fired and the tissue heat sealed simultaneously with cutting. Typically, the cutting element is heated to a temperature over 100° Celsius. However, the cutting element is usually not operated at extremely high temperatures, more than several hundred degrees Celsius, because of the possibility of damage to surrounding tissue or to the instrument.

Figure 4:
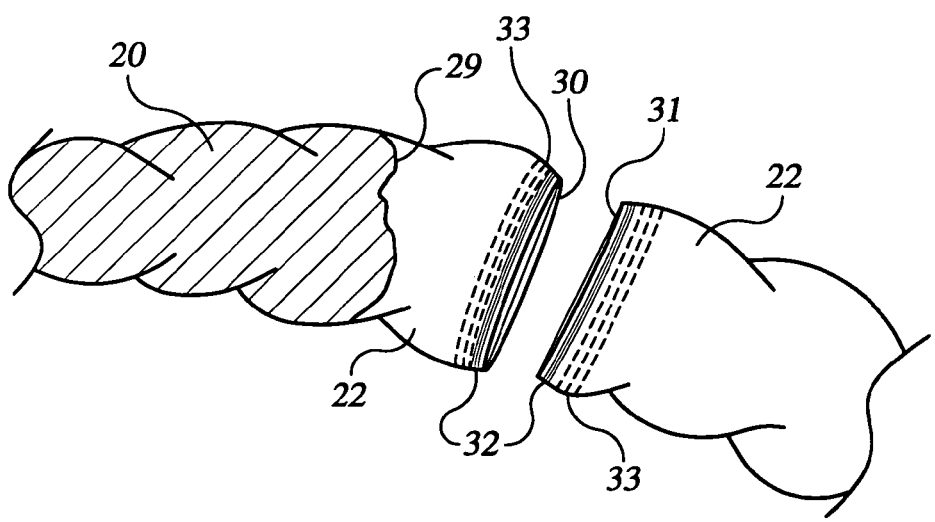
FIG. 4 shows the two large intestine ends cut and sealed.

FIG. 4 shows the two large intestine 22 ends after the cut and seal procedure. The left dissected edge 30 and right dissected edge 31 have been cauterized by the cutting action of the cutting element. Just inside the wounds are bands of cauterized tissue 32, placed there by the left and right sealing elements. These bands of cauterized tissue seal the colon's anterior and posterior sides together, prevent bleeding, and assist in preventing waste from leaking out of the colon. Proximal to the bands of cauterized tissue 32 are three rows of surgical staples 33 that provide most of the securing force necessary to keep the colon sealed permanently. Each row of staples is slightly offset from the other. Note that additional rows of staples can be made by firing or activating the stapler multiple times or by providing a stapler with more rows of staples.

The procedure shown in FIGS. 3 and 4 is repeated on the other side of the section of diseased colon 20 along cut line 26. The diseased section of colon 20 is then removed from the patient 19. Subsequently, the two remaining healthy sections of colon are joined together to restore the flow of waste, as shown in FIGS. 5 through 8.

Figure 5:
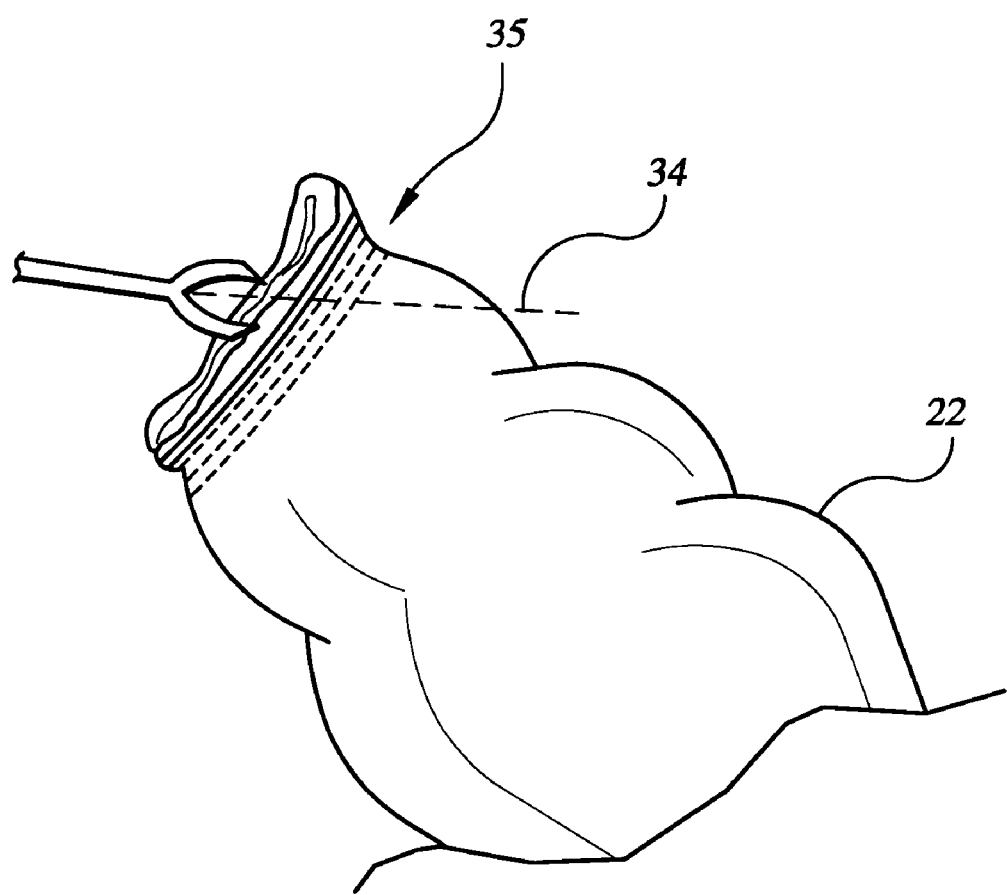
FIG. 5 shows one end of the newly cut large intestine being cut again to form a new opening in the healthy intestine.

FIG. 5 shows one end of the newly cut large intestine 22 being cut again to form a new opening in the healthy intestine. The surgeon cuts along line 34 with a standard laparoscopic cutting instrument, resulting in a diagonal opening 35 in the intestine. This procedure is repeated with the other intestine end.

Figure 6:
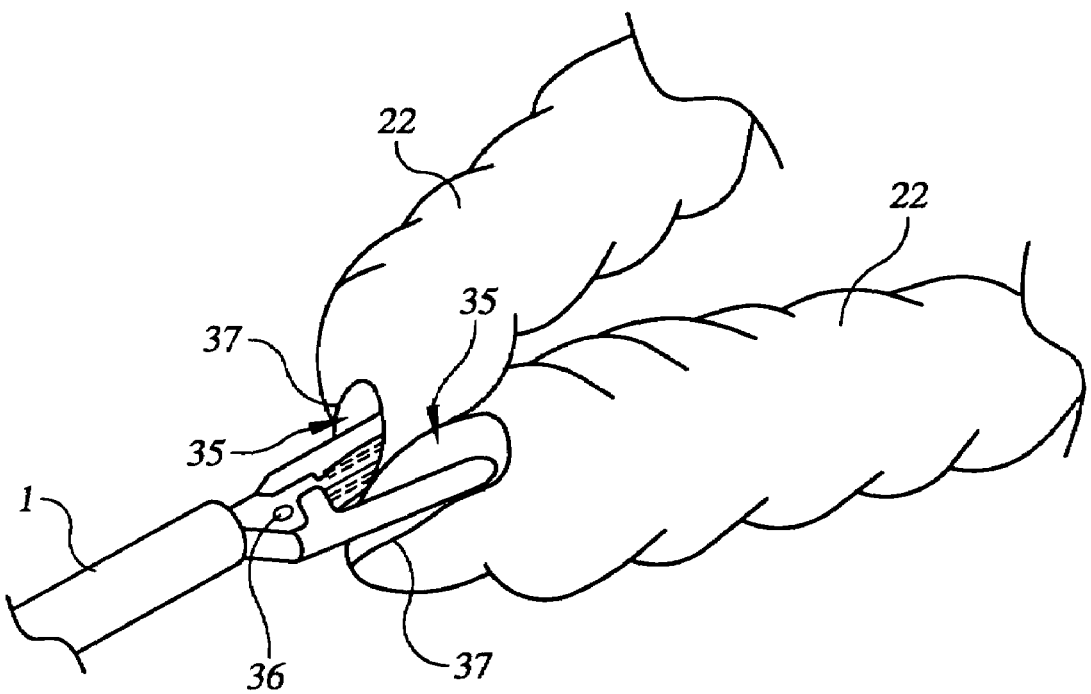
FIG. 6 shows how the two large intestine ends are joined together and then cut and sealed again.

FIG. 6 shows how the two large intestine ends are next joined together and then cut and sealed again. The two sections of colon 22 are brought together, with their open ends 35 placed next to each other as shown. The jaws of the laparoscopic dissecting instrument 1 then grip the walls of the two sections of colon such that the proximal end of the jaws 36 is placed at the edges 37 of the open colon sections. Thus, a portion of each colon section is trapped between the jaws. The jaws are then closed, the tissue cauterized, the staples fired, and the tissue cut as described above.

Figure 7:
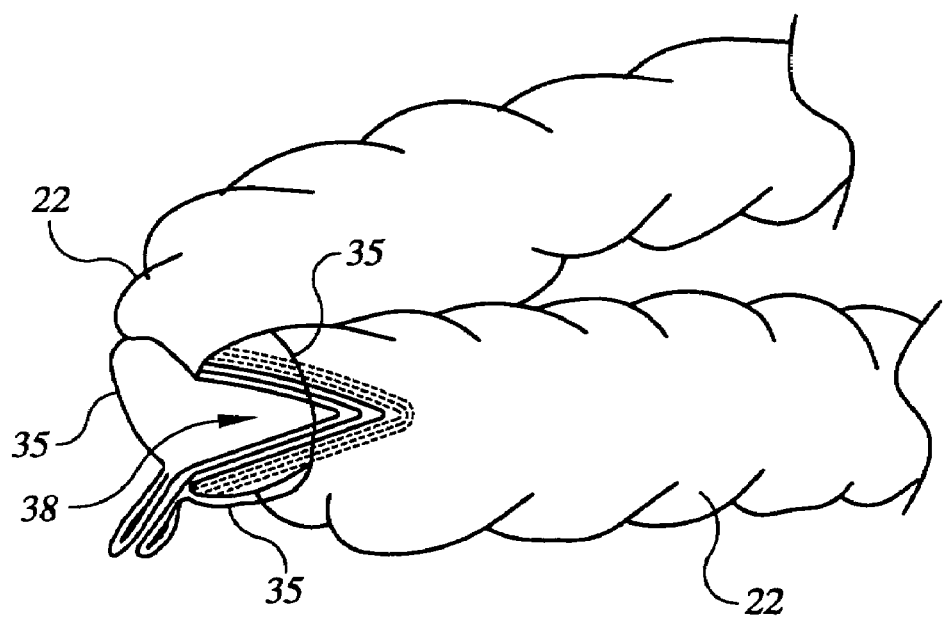
FIG. 7 illustrates the opening made by the procedure in FIG. 5.

FIG. 7 illustrates the opening made by the procedure in FIG. 6. The cut and seal procedure leaves a "V" shaped wound 38 that creates a passage between the walls of the two sections of colon 22. The passage 38 is large enough to allow waste to flow between the two sections of colon.

Figure 8:
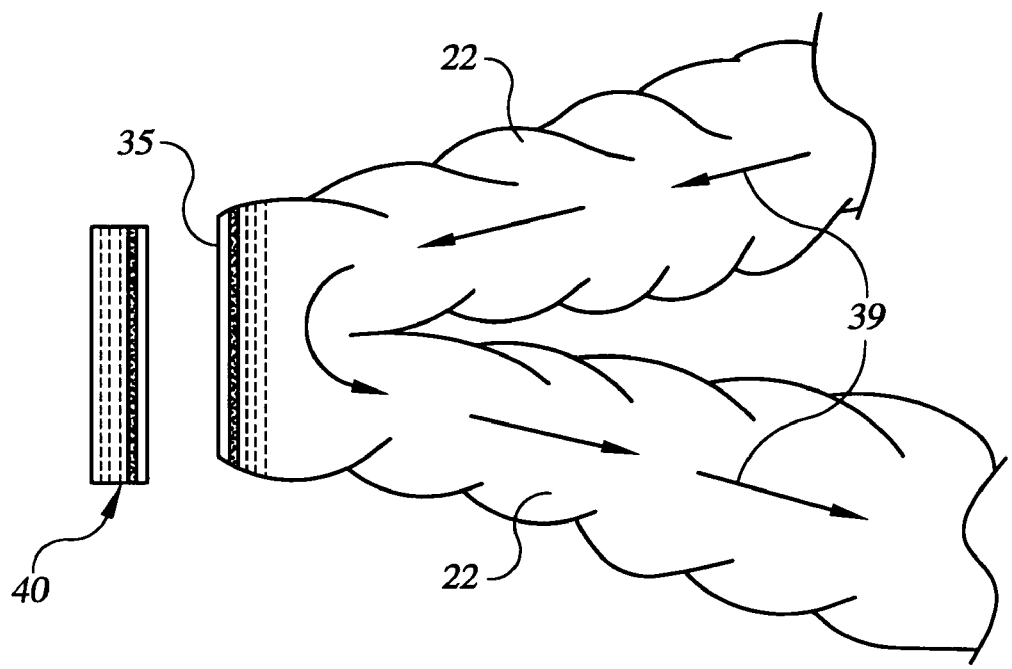
FIG. 8 shows how a third cut and seal procedure closes the two large intestine ends together, allowing the flow of waste through the newly joined colon.

FIG. 8 shows how a third cut and seal procedure closes the two large intestine 22 ends together. The open ends of the colon section 35 shown in FIG. 6 are clamped together with the jaws of the laparoscopic instrument. Then the seal, staple, and cut procedures are repeated. The result is that both colon ends are sealed together, creating a passage though which waste can flow (as shown by arrows 39). Note that a scrap of colon tissue 40 remains after this step, which is removed and discarded once the colon sections have been successfully joined.

Figure 9:
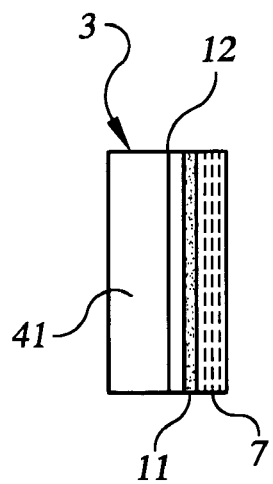
FIG. 9 illustrates a configuration for the grasping face of the inferior jaw that would leave no scrap when used.

FIG. 9 illustrates a configuration for the grasping face of the inferior jaw 3 which would leave no scrap when used in a procedure different than that shown in FIGS. 2 through 8. In this configuration, the left side 41 of the grasping face is devoid of sealing elements and staples (such as those shown in FIG. 1). Thus, no scrap remains when the right sealing element 15, right row of staples 8, and the cutting element 16 are used on the ends of the colon shown in FIG. 7. Alternatively, the same result can be obtained by using the grasping face configuration shown in FIG. 1. In this case, the surgeon fires only one set of rows of staples and uses only the sealing element next to that set of rows of staples to seal the tissue.

In addition to the configuration of staple rows, sealing elements, and cutting element shown in FIG. 9, other configurations are possible. For example, the inferior jaw 3 may be designed with opposite symmetry such that the sealing element and staples are on the left side of the cutting element 16. In another example, the placement of the heating elements and staple rows may be asymmetrical(or one of the two sealing elements may be turned off) if advantageous for a particular technique.

Figure 10:
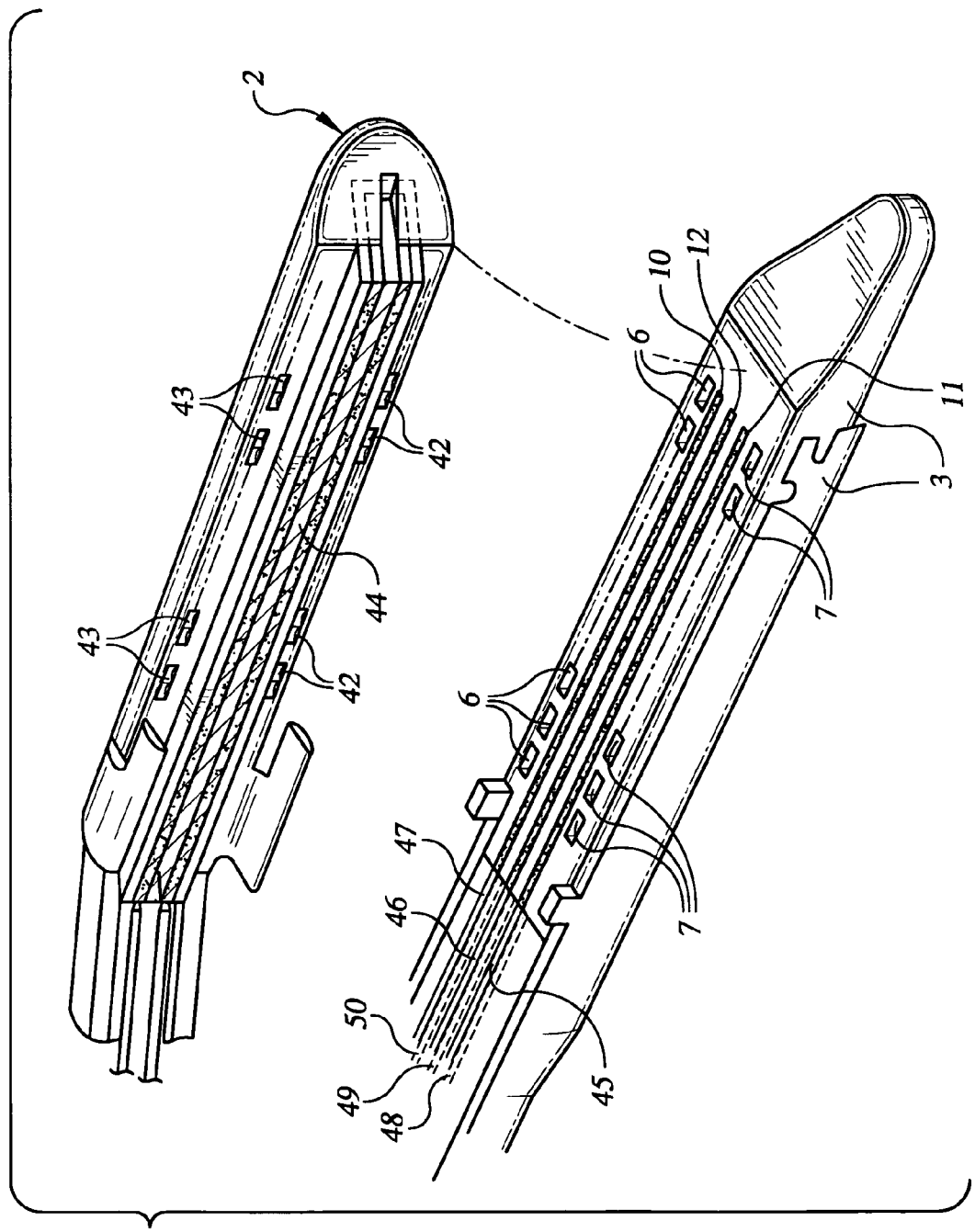
FIG. 10 illustrates in detail the grasping faces of the superior and inferior jaws.

FIG. 10 illustrates the stapling head of FIG. 1 in detail, with the superior and inferior jaws laid open relative to each other for clear illustration of detail. The stapling head comprises the first grasping face 2a, or the grasping face of the superior jaw 2 and a second grasping face 2b, or the grasping face of the inferior jaw 3. Along the right and left sides of the grasping face of the inferior jaw 3 lie two rows of staples, a left row of staples 7 and a right row of staples 8. Each row of staples comprises a series of staples oriented along the longitudinal axis of the inferior jaw 3. Each staple is comprised of a typical surgical staple. Although only two rows of staples are shown in FIG. 10, the inferior jaw 3 could easily be made wider to accommodate more rows of staples. Typically about 2 to 8 rows of staples are provided, with matching numbers of rows of staples located on either side of the inferior jaw 3. For convenience during manufacture or use, the staples may be disposed within a cartridge 52 which is further disposed in the trough-like body of the inferior jaw. This cartridge may be first loaded with staples, then inserted into the jaw. If a reusable device is desired, the cartridge may be removably attachable into the inferior jaw, so that surgeons can discharge staples to establish a joint, remove the device from the laparoscopic worksite, remove the spent cartridge and replace it with a new, loaded cartridge. If a disposable device is desired, the cartridge may be fixedly attached to the inferior jaw, or the jaw may be fabricated without a distinct cartridge (that is, the cartridge may be formed integrally with the jaw).

Along the right and left sides of the grasping face of the superior jaw 2 lay two rows of staple anvils, a right row of anvils 42 and a left row of anvils 43, comprising typical dimpled staple anvils. Each anvil is oriented along the longitudinal axis of the superior jaw 2 and aligned to match the rows of staples 7 and 8. Although only two rows of staple anvils are shown on either side of the superior jaw 2, the superior jaw could easily be made wider to accommodate more rows of staple anvils. Typically about 2 to 8 rows of staple anvils are provided, with matching numbers of rows of staple anvils located on either side of the superior jaw 2.

Disposed just inside the two rows of staples 7 and 8 on the inferior jaw 3 are two parallel rows of sealing elements, or electrically resistive wires, used to cauterize tissue. The sealing elements generally lie along the long axis of the stapler head 9, though radially offset from the long axis. The left sealing element 14 is operably connected to the power source 11 and to the left control dial 13. A right sealing element 15 is similarly connected to the power source 11 and the right control dial. To ensure that tissue is not cut when it should be sealed, both sealing elements are operably connected to the control box 12 so that neither element can heat up to a temperature exceeding a point predetermined by the manufacturer. The predetermined maximum temperature is about 99° Celsius to about 105° Celsius. The exact temperature depends on the intended application of the device, though the tissue to be sealed should not exceed a temperature of 99° Celsius.

Both sealing elements are comprised of a material with a positive temperature coefficient, a high resistance or both, such as a NiCr alloy, NiTi alloy, stainless steel, FeCr alloy, NiCrAl alloy carbon or other suitable elements and alloys available from vendors such as Wiretron. The width of the sealing elements is from about 0.008" to about 0.020". For devices intended for colectomy, the sealing elements comprise nichrome and are typically about 0.010" to about 0.012" wide. The heating elements may be provided with non-stick surface coatings.

Disposed along the long axis, or center, of the grasping face of the inferior jaw is a cutting element 16, or electrically resistive wire, used to sever tissue. The width of the cutting element is about 0.008" to about 0.020", depending on the application, and is made of the same materials as the sealing elements. For devices intended for colectomies the cutting element is typically about 0.010", wide to about 0.012" wide. The cutting element 16 is operably connected to the power source 11 and a control dial 17 that controls the temperature of the cutting element 16. The temperature of the cutting element 16 is designed to operate at a temperature of about 100° Celsius to several hundred degrees Celsius. However, to prevent damage to the device and to surrounding tissue, an electrical control mechanism prevents the temperature of the cutting element 16 from exceeding about 580° Celsius.

For all three heating elements the temperature is measured with thermocouples or thermistors disposed in proximity to the heating elements, and the heating elements are controlled by adjusting the current flow or voltage through the elements in response to the measured temperature of the elements. Alternatively, other measurement schemes could be used, such as measuring the radiant heat from the elements or measuring the temperature of the grasping face proximate the heating elements, or directly measuring the temperature of the tissue trapped between the jaws during use.

Located in the center of the grasping face of the superior jaw 2, and sized to accommodate all three heating elements 14, 15, and 16, is a resilient anvil 44 that runs along the longitudinal axis of the superior jaw 2. The resilient anvil 44 is made of a substantially resilient, non-stick material that is thermally resistant (stable at high temperatures). Suitable materials include polytetrafluoroethylene (PTFE) (available as Teflon®), graphite, Kapton®, mica, or silicone. The resilient anvil 44 evens out pressure against tissue and insulates the superior jaw 2 electrically and thermally. The anvil 44 also prevents heat dissipation and focuses heat from the three heating elements on specific areas of tissue, thus helping to prevent damage to surrounding tissues. However, within the local area of the sealing or cutting elements, the resilient anvil 44 helps to spread heat evenly on the tissue intended to be cut or sealed. In addition, the resilient anvil 44 may incorporate thermally reflective material, or material with low thermal conductivity, as layers or coatings. Useful reflecting or low thermal conductivity materials include ceramics, thermally reflective metals, and thermally reflective polymers, such as Mylar® polymeric compositions. By insulating and reflecting the heat generated by the heating elements, the coated resilient anvil 44 minimizes power consumption and further limits heating of surrounding tissue.

At the proximal end of the inferior jaw 3 are a right power conductor 45, a middle power conductor 46, and a left power conductor 47 that conduct electrical power from the power source 11 to the three heating elements, 14, 15, and 16. Inferior to the power conductors, shown in shadow, are a right ground wire 48, a middle ground wire 49, and a left ground wire 50 that connect the heating elements to ground.

Figure 11:
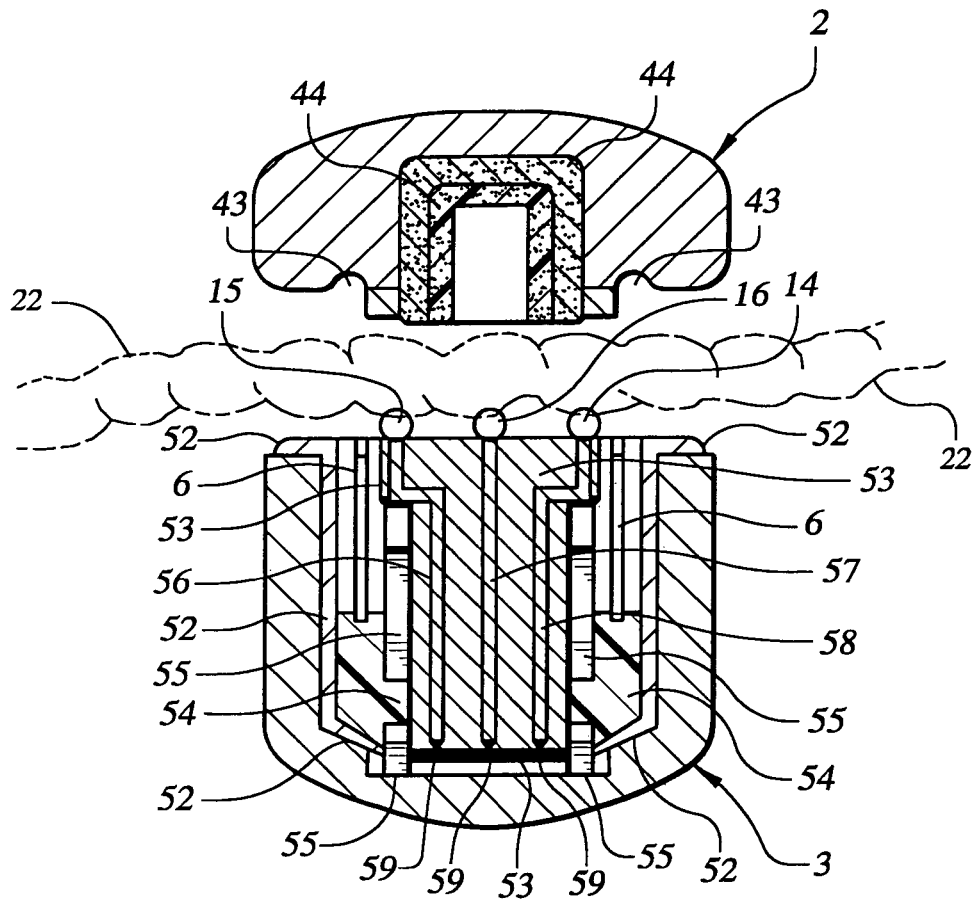
FIG. 11 shows a cross section of the superior and inferior jaws when clamped together on a section of large intestine.

FIG. 11 shows a cross section of the superior jaw 2 and inferior jaw 3 clamped together on a section of large intestine 22. The cross section is taken at the point where the three heating elements terminate at the distal end of the inferior jaw 3. For reference, the resilient anvil 44 and the staple anvils 43 are shown in cross section. Also visible from this perspective is a cartridge 52, which fits snugly into the inferior jaw 3.

The cartridge 52 comprises a heating element support 53, that is an integral part of the cartridge; two rows of staple drivers 54, which are operably disposed within actuator wedge channels 55; a series of staples 7 disposed superior to the staple drivers 54; and the three heating elements 14, 15, and 16, which are securely attached to the superior side of the heating element support 53. If provided in releasably attachable form, the cartridge 52 allows the staples 7 and heating elements 14, 15, and 16 to be easily replaced after the surgeon uses the cartridge 52. The surgeon simply removes the laparoscopic dissecting instrument from the patient and replaces the used cartridge with a fresh cartridge. Each fresh cartridge is loaded with staples and carries new heating elements.

The heating element support 53 is made of a thermal insulator but, unlike the resilient anvil 44, the heating element support 53 is made from a relatively hard substance so that the three heating elements are supported when the jaws, 2 and 3, grip tissue. The heating element support 53 is made from polyamide coated with non-stick Teflon® backed by steel, carbon, ceramics, mica, Teflon®, fiberglass composite, Kevlar® composite, or other non-electrically insulating material with a high dielectric constant. The heating element support 53 is sized and proportioned to be at the same height as the inferior jaw when the cartridge is fully inserted. Thus, the jaws can maintain a tight grip when closed. In alternate configurations, the heating element support 53 may be disposed higher than the grasping face of the lower jaw to accommodate bulky tissue.

The three heating elements are electrically connected to ground wires. Each heating element 14, 15, and 16 is respectively electrically connected to the right ground wire 56, the central ground wire 57, and the left ground wire 58. Ground is conducted through wires 56, 57, and 58, which pass through cartridge along channels 59 in the inferior portion of the heating element support, across the contacts in the inferior jaw 3 to ground wires 48, 49, and 50 running through the laparoscopic dissecting instrument 1, and ultimately to the power supply 11.

The heating elements are placed in electrical contact with the conducting wires whenever a cartridge is inserted into the inferior jaw 3. Likewise, the ground wires in the cartridge are placed in electrical contact with the insulated ground wires 48, 49, and 50 whenever a cartridge is inserted into the inferior jaw 3.

Figure 12:
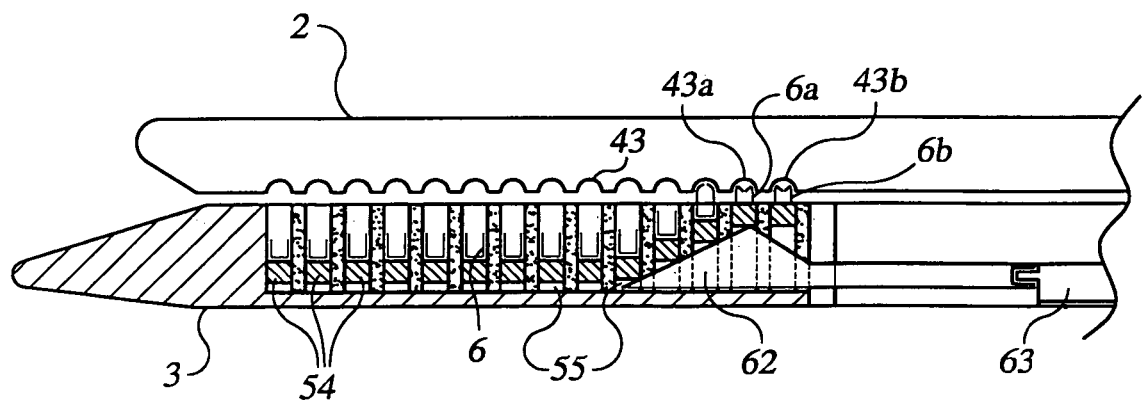
FIG. 12 a cross section of the inferior jaw and superior jaw and shows the action of the actuator wedges.

FIG. 12 illustrates a cross section of the inferior jaw 3 and superior jaw 2 and shows the action of the actuator wedges 62. The actuator wedges 62 are operably connected to the stapler lever 10 by a drive rod 63. When stapler lever 10 is depressed the drive rod 63 forces the actuator wedges 62 into the actuator wedge channels 55. As the actuator wedges 62 enter the channels 55 the actuator wedges force each succeeding staple driver 54 towards the staple openings. This, in turn, causes the staples 7 to drive in succession through the tissue of the colon and into the staple anvils 43 of the superior jaw 2. The staples then deform under pressure, molded by the anvils to grasp the colon tissue. The process is illustrated by staples 6a and 6b being molded into anvils 43a and 43b. The result is that the staples join the two sides of the colon together, just as one would staple two pieces of paper together.

Figure 13:
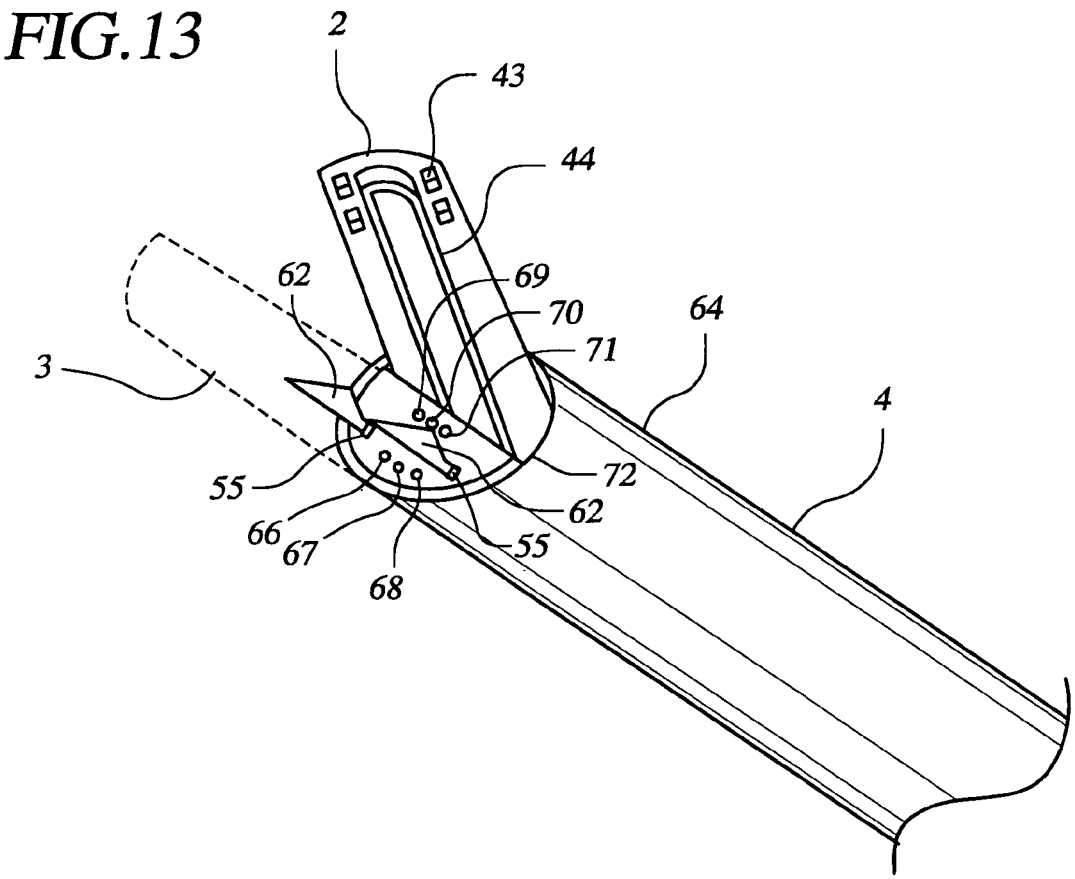
FIG. 13 illustrates the distal tip of the proximal handle.

FIG. 13 shows a view of the distal tip 64 of the proximal handle 6 and the grasping face of the superior jaw 2. The staple anvils 43 and resilient anvil 44 are shown for reference. In this view, the inferior jaw 3 is shown in shadow in order to illustrate the actuator wedges 62 and electrical contacts. To facilitate the ease of snapping the disposable cartridge 52 into the inferior jaw 3, the actuator wedges 62 can be fully withdrawn into the wedge channel 55 unless the stapler lever 10 is depressed.

Also shown in FIG. 13 are a set of electrical ground contacts, comprising a right ground contact 66, a central ground contact 67, and a left ground contact 68. Each of these contacts are placed respectively in contact with the ground wires 45, 46, and 47 when the disposable cartridge is inserted into the inferior jaw. Likewise, the electrical power contacts comprise a right power contact 69, a central power contact 70, and a left power contact 71. Each of these contacts are placed respectively in contact with heating elements 14, 15, and 16 when the disposable cartridge is inserted into the inferior jaw.

Typically, the inferior jaw 3 is a permanent part of the distal tip 64 of the laparoscopic dissecting instrument 1 and the disposable cartridge 52 is removably attached to a channel formed in the inferior jaw 3. However, from the perspective in FIG. 11 one can see that the entire inferior jaw may be modified to be removably attached to the distal tip 64 of the instrument 1. Thus, the entire inferior jaw 3 would comprise the disposable cartridge. In this case the distal end of the instrument is fitted with a cartridge channel 72. The cartridge channel has a securing means such that the inferior jaw may be removably, but securely snapped into place. The electrical contacts and actuator wedge channels 55 of the inferior jaw would align with the distal tip 64 of the instrument to allow operation of the device.

Figure 14:
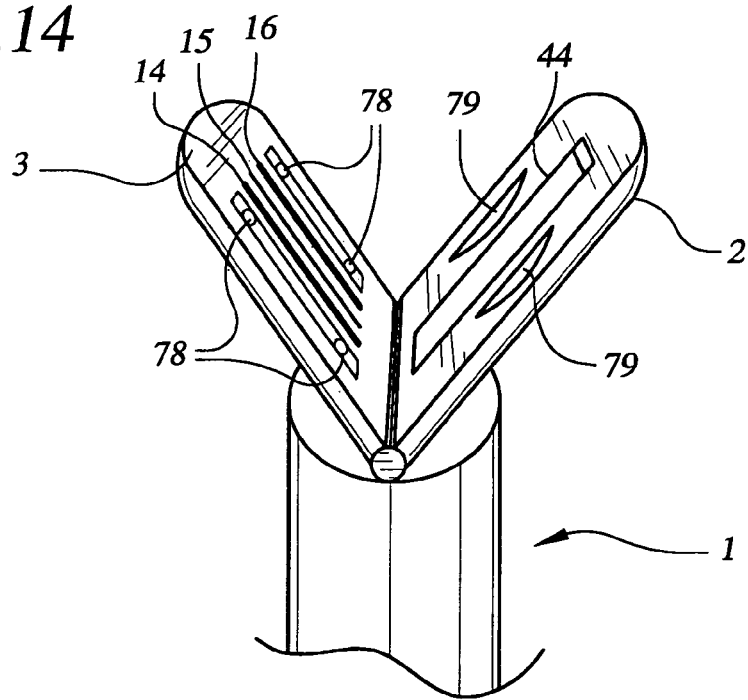
FIG. 14 illustrates the grasping faces of the superior and inferior jaws for a version of the laparoscopic dissecting instrument modified to clip smaller body lumens.

FIG. 14 illustrates the grasping faces of the superior jaw 2 and inferior jaw 3 of a version of the laparoscopic dissecting instrument 1 modified to clip smaller body lumens. The resilient anvil 44, left 14 sealing element, right sealing element 15, and cutting element 16 are shown for reference. Clips 78 replace the staples and the entire instrument 1 is sized appropriately for a targeted lumen, typically a blood lumen. The superior jaw 2 is modified so that the two rows of staple anvils comprise two rounded anvils 79. As with the stapling instrument, the width of the jaws may be increased to accommodate additional clips and clip anvils. Typically one to three clips and clip anvils are provided on each side of the heating elements. The adapted laparoscopic dissecting instrument 1 may be used with a variety of surgical techniques where blood lumens are ligated and cut. Example techniques include vein harvest, the Linton procedure, renal artery surgery, liver surgery, and splenectomies.

Figure 15:
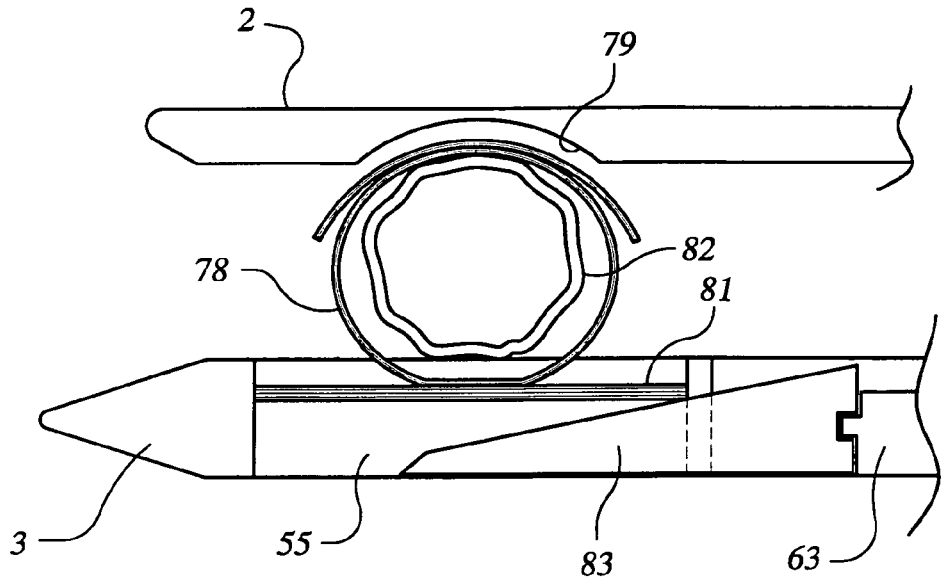
FIG. 15 illustrates a cross section of the modified instrument shown in FIG. 14.

FIG. 15 illustrates a cross-section of the modified laparoscopic dissecting instrument 1 being used to clip a blood lumen. The principal of operation is the same as with the stapling instrument. The inferior jaw 3 is modified so that it contains only two clips 78 and two parallel clip drivers 81. The lumen 82 to be cut and sealed is placed between the two clip ends and then the stapler lever 10 is depressed. Depressing the stapler lever 10 causes the drive rod 63 to force modified actuator wedges 83 into the wedge channels 55. The actuator wedges 83 drive the clip drivers 81 upwards. In turn, the clip drivers force the two clips 78 into the anvils 79 such that the clips will deform to squeeze and seal off the lumen 82. Afterwards, the lumen is thermally sealed and cut as described above for sealing and cutting the colon.

Figure 16:
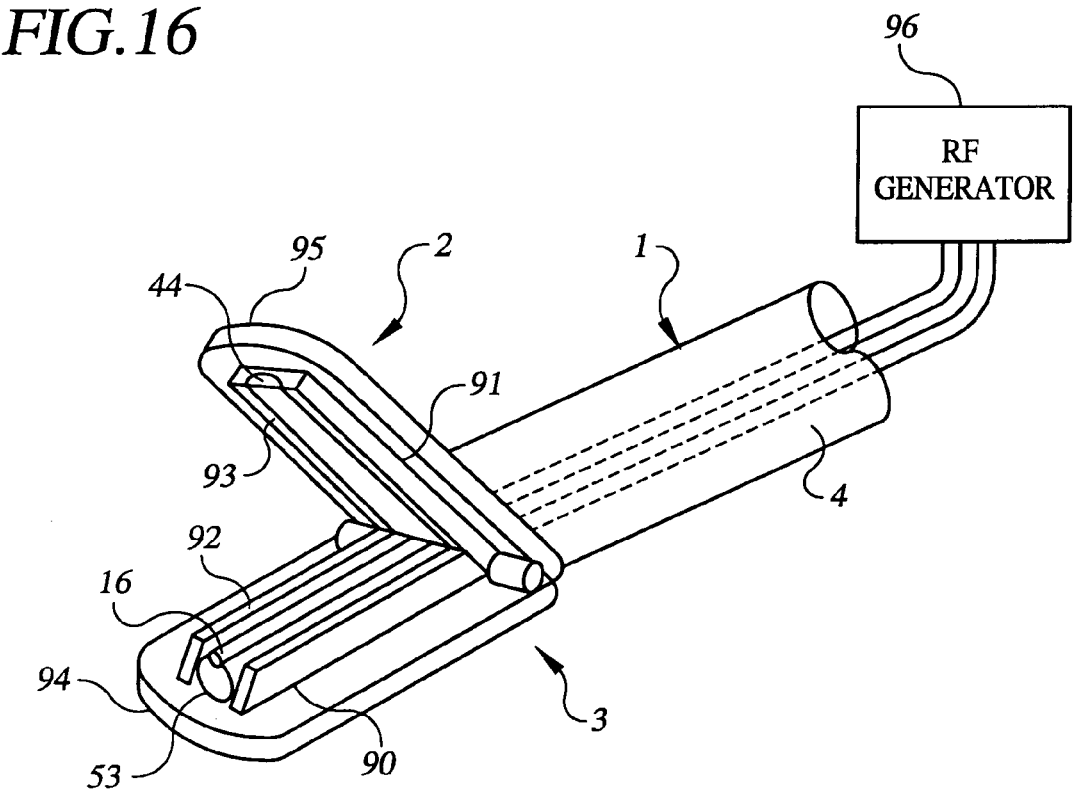
FIG. 16 shows an embodiment of the laparoscopic dissecting instrument with bipolar RF electrodes for sealing elements.

FIG. 16 shows an embodiment of the laparoscopic dissecting instrument 1 with bipolar RF electrodes 90, 91, 92 and 93 for sealing elements. The bipolar electrodes are suitable for transmitting RF energy at power levels sufficient to seal tissue. The superior jaw 2 and the inferior jaw 3 each have matching pairs of bipolar electrodes disposed on the jaws. A cutting element 16 is disposed on the firm, thermally insulating cutting element support 53 in the inferior jaw. A resilient, thermally insulating anvil 44, suitable for receiving and meeting the cutting element and intervening tissue when the jaws close, is disposed in the superior jaw. Insulating housings 94 and 95 cover the outer surfaces of the jaws and protect tissue external to the operation site. The features described above in relation to FIGS. 1 and 10 through 15 may be incorporated into the device illustrated in FIG. 16, such as the staple cartridge and proximal operating mechanisms, and the cartridge may include the staples and staple driver and the cutting element and heating elements as illustrated in relation to the resistive heating embodiments.

Electrode 90 on the inferior jaw and electrode 91 on the superior jaw are operably paired, through RF generator 96, to operate as bipolar electrodes. Likewise, electrode 92 on the inferior jaw and electrode 93 on the superior jaw are operably paired through the RF generator to operate as bipolar electrodes. Suitable conductors run through the insertion rod 4 to the RF generator 96 which is operable to provide RF power in the range of about 475 kHz, at power levels of about 50 to about 500 watts. Different power levels may be appropriate for devices intended for distinctly different surgeries. The electrodes are disposed on opposing grasping faces of the inferior and superior jaws so that closure of the jaws brings the electrodes into opposing relationship. When tissue is trapped between the jaws heating element 16 is operated to divide the tissue, and electrode pairs 90 and 91, and 92 and 93, are operated in bipolar fashion to seal the divided tissue.

The sealing elements may also comprise monopolar, ultrasound heating elements, or microwave heating elements. Whatever the technology used, the sealing elements are capable of raising the target tissue to a temperature sufficient to seal the tissue and cauterize bleeding blood vessels.

In other embodiments the cutting element may comprise a monopolar electrode disposed in the superior and inferior jaws. In this case, the monopolar electrodes are suitable for transmitting RF energy sufficient to sever tissue. In addition, the cutting and sealing elements may also comprise microwave or ultrasonic elements suitable for cutting or sealing tissue, respectively. The control mechanisms may also be designed, or additional control mechanisms added, to provide appropriate monopolar RF, microwave, or ultrasonic energy to the cutting or sealing elements if these alternative technologies are used. In still other embodiments the jaws of the dissecting instrument may be provided with one or more rows of staples and matching rows of staple anvils in the opposing jaw. In yet other embodiments the sealing elements or rows of staples may be disposed on only one side of the cutting element, as described in relation to FIG. 9.

While the preferred embodiments of the devices and methods have been described in reference to the environment in which they were developed, they are merely illustrative of the principles of the inventions. While the colectomy operation serves to illustrate the devices and methods which may be accomplished with the devices, many other surgical procedures may be accomplished with the device, such as laparoscopic appendectomy (for transection of the appendix), laparoscopic cholecystectomy (gall bladder removal), laparoscopic esophagectomy, laparoscopic splenectomy (for transection of the splenic hilum), hysterectomies, umbilical cord separation and various laparoscopic biopsies and artery transections and dissections. Thus various lumens of the body may be dissected and ligated with the devices, and various organs, when disease or trauma requires, may be removed with the devices. Other embodiments and configurations may be devised without departing from the spirit of the inventions and the scope of the appended claims.

I claim:

1. A method of cutting and sealing tissue comprising the steps of:
    providing a device for cutting and sealing tissue comprising:
        an insertion rod;
        a first jaw and a second jaw extending from the insertion rod, said first and second jaws being operable to allow closure of the first and second jaws relative to each other, said first jaw having a first grasping face and said second jaw having a second grasping face, said first grasping face and said second grasping face aligned to meet each other upon closure of the first and second jaws;
        a cutting element comprising an electrically resistive wire disposed in the first jaw and further disposed along the longitudinal axis of the insertion rod;
        a first electrode disposed on the first jaw, said first electrode operably paired with a second electrode disposed on the second jaw, said first and second electrodes aligned to face each other upon closure of the first and second jaws, said first and second electrodes laterally spaced from and parallel to the longitudinal axis of the insertion rod, and said first and second electrodes operable as bipolar electrodes;
        a third electrode disposed on the first jaw, said third electrode operably paired with a fourth electrode disposed on the second jaw, said third and fourth electrodes aligned to face each other upon closure of the first and second jaws, said third and fourth electrodes laterally spaced from and parallel to the longitudinal axis of the insertion rod, said third electrode disposed opposite the first electrode and said fourth electrode disposed opposite the second electrode, and said third and fourth electrodes operable as bipolar electrodes;
    grasping tissue between the first and second grasping faces;
    transmitting RF energy to the bipolar electrodes at energy levels sufficient to seal tissue; and
    adjusting the temperature of the cutting element to a temperature above about 100° Celsius until the tissue is severed.

2. The method of claim 1 wherein the tissue is a section of the intestines.

3. The method of claim 1 wherein the tissue comprises a diseased body organ.

4. The method of claim 1 wherein the tissue comprises an injured body organ.

5. A device for cutting and sealing body tissue comprising:
    an insertion rod;
    a first jaw and a second jaw extending from the insertion rod, said first and second jaws being operable to allow closure of the first and second jaws relative to each other, said first jaw having a first grasping face and said second jaw having a second grasping face, said first grasping face and said second grasping face aligned to meet each other upon closure of the first and second jaws;
    a first cutting element comprising a first monopolar electrode disposed on the first jaw;
    a second cutting element comprising a second monopolar electrode disposed on the second jaw;
    a first electrode disposed on the first jaw, said first electrode operably paired with a second electrode disposed on the second jaw, said first and second electrodes aligned to face each other upon closure of the first and second jaws, said first and second electrodes laterally spaced from and parallel to the longitudinal axis of the insertion rod, and said first and second electrodes operable as bipolar electrodes;

a third electrode disposed on the first jaw, said third electrode operably paired with a fourth electrode disposed on the second jaw, said third and fourth electrodes aligned to face each other upon closure of the first and second jaws, said third and fourth electrodes laterally spaced from and parallel to the longitudinal axis of the insertion rod, said third electrode disposed opposite the first electrode and said fourth electrode disposed opposite the second electrode, and said third and fourth electrodes operable as bipolar electrodes.

6. The device of claim 5 further comprising an RF generator for supplying RF energy to the first and second cutting elements and the first, second, third, and fourth electrodes.

7. A method of cutting and sealing tissue comprising the steps of:

providing a device for cutting and sealing tissue comprising:

an insertion rod;

a first jaw and a second jaw extending from the insertion rod, said first and second jaws being operable to allow closure of the first and second jaws relative to each other, said first jaw having a first grasping face and said second jaw having a second grasping face, said first grasping face and said second grasping face aligned to meet each other upon closure of the first and second jaws;

a first cutting element comprising a first monopolar electrode disposed on the first jaw;

a second cutting element comprising a second monopolar electrode disposed on the second jaw;

a first electrode disposed on the first jaw, said first electrode operably paired with a second electrode disposed on the second jaw, said first and second electrodes aligned to face each other upon closure of the first and second jaws, said first and second electrodes laterally spaced from and parallel to the longitudinal axis of the insertion rod, and said first and second electrodes operable as bipolar electrodes;

a third electrode disposed on the first jaw, said third electrode operably paired with a fourth electrode disposed on the second jaw, said third and fourth electrodes aligned to face each other upon closure of the first and second jaws, said third and fourth electrodes laterally spaced from and parallel to the longitudinal axis of the insertion rod, said third electrode disposed opposite the first electrode and said fourth electrode disposed opposite the second electrode, and said third and fourth electrodes operable as bipolar electrodes.

grasping tissue between the first and second grasping faces;

transmitting RF energy to the bipolar electrodes at energy levels sufficient to seal tissue; and transmitting RF energy to the first and second cutting elements at energy levels sufficient to cut tissue.

8. The method of claim 7 wherein the body tissue is a section of the intestines.

9. The method of claim 7 wherein the tissue comprises a diseased body organ.

10. The method of claim 7 wherein the tissue comprises an injured body organ.

11. A method of cutting and sealing tissue comprising the steps of:

providing a device for cutting and sealing tissue comprising:

an insertion rod;

a first jaw and a second jaw extending from the insertion rod, said first and second jaws being operable to allow closure of the first and second jaws relative to each other, said first jaw having a first grasping face and said second jaw having a second grasping face, said first grasping face and said second grasping face aligned to meet each other upon closure of the first and second jaws;

a cutting element comprising an electrically resistive wire disposed in the first jaw and further disposed along the longitudinal axis of the insertion rod;

a first electrode disposed on the first jaw, said first electrode operably paired with a second electrode disposed on the second jaw, said first and second electrodes aligned to face each other upon closure of the first and second jaws, said first and second electrodes laterally spaced from and parallel to the longitudinal axis of the insertion rod, and said first and second electrodes operable as bipolar electrodes;

a third electrode disposed on the first jaw, said third electrode operably paired with a fourth electrode disposed on the second jaw, said third and fourth electrodes aligned to face each other upon closure of the first and second jaws, said third and fourth electrodes laterally spaced from and parallel to the longitudinal axis of the insertion rod, said third electrode disposed opposite the first electrode and said fourth electrode disposed opposite the second electrode, and said third and fourth electrodes operable as bipolar electrodes.

grasping tissue between the first and second grasping faces;

transmitting electrical energy to the bipolar electrodes at energy levels sufficient to seal tissue; and operating the cutting element to severe the tissue.

12. The method of claim 11 wherein the tissue comprises a lumenal vessel of the body.

* * * * *